United States Patent [19]

Peck

[11] Patent Number: 4,834,841

[45] Date of Patent: May 30, 1989

[54] METHOD FOR TREATING BAKING OVEN STACK GASES

[76] Inventor: Kenneth W. Peck, 13725 SW. 78 Ct., Miami, Fla. 33158

[21] Appl. No.: 103,299

[22] Filed: Oct. 1, 1987

[51] Int. Cl.$^4$ .................... B01D 3/14; B01D 5/00; B01D 15/00; C07C 29/80

[52] U.S. Cl. .................... 203/19; 203/25; 203/27; 203/41; 203/100; 203/DIG. 8; 203/DIG. 13; 55/97; 55/269; 126/300; 202/176; 202/202; 210/673; 210/677; 568/916

[58] Field of Search .................... 203/19, DIG. 13, 41, 203/40, DIG. 8, 21, 25, 27, 100; 55/269, 97, 80, 62; 426/486, 523; 568/913, 916; 210/673, 677; 202/176, 182, 202, 163, 153; 126/300, 299 R, 301

[56] References Cited

U.S. PATENT DOCUMENTS

| | | | |
|---|---|---|---|
| 1,577,534 | 3/1926 | Miller | 55/269 |
| 2,743,529 | 5/1956 | Hayes | 126/299 R |
| 3,122,486 | 2/1964 | Skarstrom | 203/41 |
| 3,124,438 | 3/1964 | Lavery | 55/62 |
| 3,151,607 | 10/1964 | Brouillard | 126/299 R |
| 3,369,371 | 2/1968 | Holly et al. | 62/54 |
| 3,396,515 | 8/1968 | Wright | 55/269 |
| 3,729,387 | 4/1973 | Naschke et al. | 203/19 |
| 3,762,394 | 10/1973 | Newcomer | 126/300 |
| 3,890,207 | 6/1975 | Chapman et al. | 203/DIG. 8 |
| 3,963,466 | 6/1976 | Hynes | 55/269 |
| 4,101,299 | 7/1978 | Bertucci | 55/269 |
| 4,110,091 | 8/1978 | Daeschler et al. | 62/54 |
| 4,126,000 | 11/1978 | Funk | 60/648 |
| 4,216,903 | 8/1980 | Giuffre | 126/299 R |
| 4,265,088 | 5/1981 | Funk | 60/648 |
| 4,266,958 | 5/1981 | Cummings | 62/20 |
| 4,294,664 | 10/1981 | Anthony | 203/19 |
| 4,331,690 | 5/1982 | Bradshaw | 426/233 |
| 4,362,751 | 12/1982 | Dogliotti | 426/94 |
| 4,377,443 | 3/1983 | Tuck et al. | 203/8 |
| 4,407,662 | 10/1983 | Ginder | 55/33 |
| 4,454,100 | 6/1984 | Faatz | 423/210 |
| 4,484,451 | 11/1984 | Darm | 55/269 |
| 4,556,460 | 12/1985 | Robertson et al. | 203/19 |
| 4,608,065 | 8/1986 | Lai | 55/269 |
| 4,616,562 | 10/1986 | Kuechler | 126/299 R |

*Primary Examiner*—Wilbur Bascomb
*Attorney, Agent, or Firm*—Vinson & Elkins

[57] ABSTRACT

The improved method and apparatus treats the stack gases from a commercial bakery oven to remove and recover pollutants, specifically ethyl alcohol. The method includes the steps of cooling the stack gases and passing the cooled gases through a packed column to condense the water and ethyl alcohol and if the ethyl alcohol is to be recovered drying the ethyl alcohol by distillation and by absorption of the water therefrom by a molecular sieve. The apparatus includes blowers and controls to maintain the normal flow of gases from the oven so that the removal and recovery of the ethyl alcohol from the stack gases does not interfere or change the baking conditions of the oven. This may be accomplished by a system of dampers or by controlling the discharge rate of the blowers used.

11 Claims, 4 Drawing Sheets

METHOD FOR TREATING BAKING OVEN STACK GASES

BACKGROUND

The present invention relates to an improved method and apparatus for removing and recovering certain pollutants from the gases discharged from ovens such a ovens used to bake bread and other similar products.

In 1977 Congress passed the Clean Air Act and the Ozone Ambient Air Quality Standard was a part of such act. This pollution problem was being considered by the baking industry in 1977 and the EPA was attempting to take action at that time against a Los Angeles, Calif. major bakery.

An article in the publication "Bakery" dated November, 1986, page 20 and 21 explains the generation of ethyl alcohol during the baking process and its release from the oven to the atmosphere during baking. The EPA considers ethyl alcohol to be a volatile organic chemical which is a precursor of ground-level ozone.

Considerable effort has been made since the aforementioned act to prevent the discharge of the ethyl alcohol to the atmosphere and also to attempting to write regulations which would not totally destroy the wholesale baking industry.

U.S. Pat. No. 3,369,371 discloses a process for the condensation of hydrocarbon vapors from a storage tank and their return to the tank so that the vapors are saved and the atmosphere pollution is eliminated. The vapors leaving the tank are compressed, cooled and returned to the tank.

U.S. Pat. No. 4,110,091 discloses the process of handling vapors discharged from a gasoline tank when gasoline is discharged into the tank. This process includes the cooling of the gaseous mixture to condense out the gasoline and water from the air (purifying the air) and the separation of the water from the gasoline to recover the potentially lost gasoline.

U.S. Pat. Nos. 4,126,600 and 4,265,088 disclose processes of recovering heat from exhaust gases and removing harmful, less volatile components and involves the step of subliming or "freezing out" of such components.

U.S. Pat. No. 4,266,958 discloses a process of dehydrating gaseous hydrocarbon mixture containing water, using methanol as the dehydration agent and separately recovering the hydrocarbons and water.

U.S. Pat. No. 4,294,664 discloses a process for condensing a volatile constituent of a liquid product and capturing the latent heat of condensation. The process has application to ethanol vapor obtained from a boiling mixture of wort and water. The process efficiently boils the mixture by harnessing the latent heat of condensation of ethanol in a latent heat recovery system.

U.S. Pat. No. 4,407,662 discloses the method of removing water from ethanol utilizing a desiccant bed of molecular sieves.

U.S. Pat. No. 4,454,100 discloses a process for condensation and separation of air pollutants from waste gases specifically from flue gases from industrial processes.

U.S. Pat. No. 4,556,460 discloses a method for dewatering an alcohol water solution which involves contacting the solution with a carrier gas to vaporize a portion of the solution, passing the gas and vapors through a sorbent which sorbs the water vapor in preference to the alcohol or ethanol vapor and collecting the concentrated alcohol from the carrier gas.

SUMMARY

The present invention relates to an improved method and apparatus for treating the stack gases from a commercial bakery oven to remove and recover a pollutants, specifically ethyl alcohol. The method includes the steps of cooling the stack gases and passing the cooled gases through a packed column to condense the water and ethyl alcohol which is thereafter separated into water and ethyl alcohol by one of several steps. The apparatus includes blowers and controls to maintain the normal flow of gases from the oven so that the removal and recovery of the ethyl alcohol from the stack gases does not interfere or change the baking conditions of the oven. This may be accomplished by a system of dampers or by controlling the discharge rate of the blowers used.

An object of the present invention is to provide an improved method and apparatus for removing ethyl alcohol from the stack gases of a commercial bakery oven efficiently.

Another object is to provide an improved method and apparatus for removing ethyl alcohol from the stack gases of a commercial bakery oven and recovering the ethyl alcohol to provide an income offsetting the expense of removing such pollutant from the stack gases.

A further object is to provide an improved method and apparatus for removing ethyl alcohol from a commercial bakery oven stack gases which complies with all rules regarding the limitations on discharge of pollutants into the atmosphere.

Still another object is to provide an improved method and apparatus for removing ethyl alcohol from the stack gases of a commercial bakery oven without interfering with the operating conditions in the oven.

BRIEF DESCRIPTION OF THE DRAWINGS

These and other objects and advantages of the present invention are hereinafter set forth and explained with reference to the drawings wherein.

DESCRIPTION OF THE PREFERRED EMBODIMENTS

Figure 1:
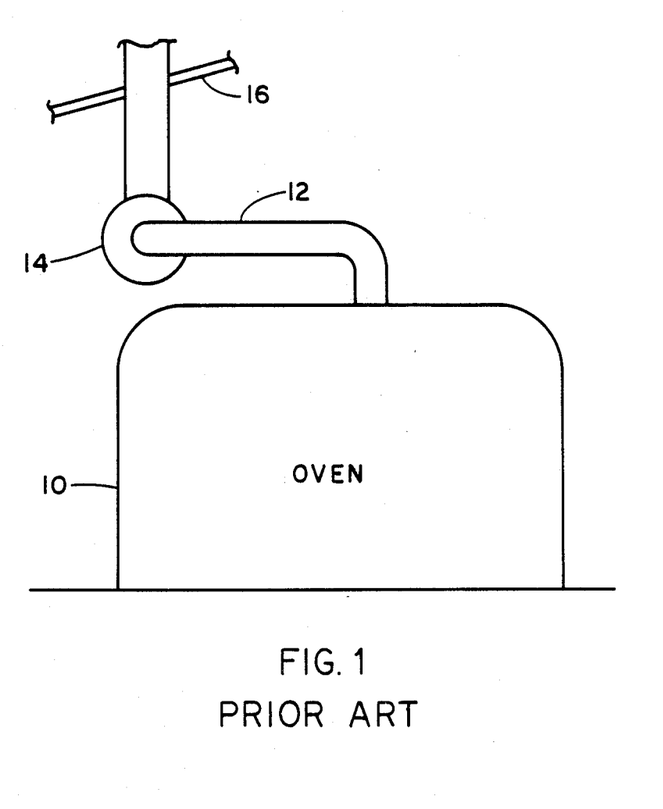
FIG. 1 is a schematic representation of a portion of a prior art commercial bakery oven in which the ethyl alcohol pollutant generated in the baking process is discharged from the oven through the stack into the atmosphere.

As shown in FIG. 1, commercial bakery oven 10, such as a bread baking oven, are generally housed within a building and the stack gases are directed from the oven 10 through stack 12, blower 14 and exhausted to the atmosphere through the roof 16. As explained, the constituents in such stack gases include ethyl alcohol (or ethanol) which is now considered to be an atmospheric pollutant and the emission of such pollutant is not considered acceptable.

Figure 2:
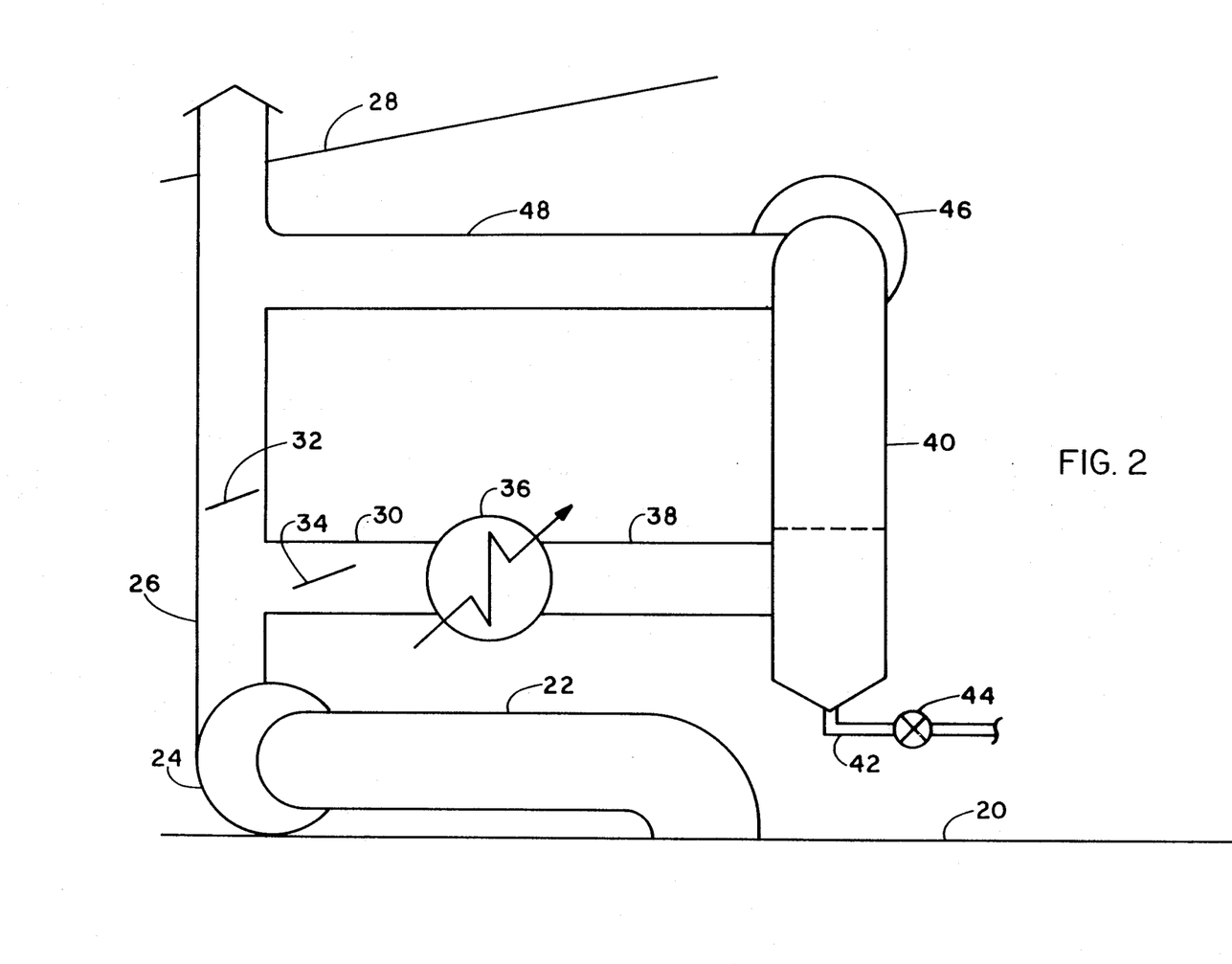
FIG. 2 is a schematic representation of the installation of one form of the improved process of the present invention on an existing commercial oven bakery oven stack.

The ethyl alcohol pollutant is removed from the stack gases by the improved method and apparatus of the present invention as shown in FIG. 2. The existing oven 20 includes stack 22, stack blower 24 and blower discharge duct 26 which discharges to the atmosphere above roof 28. Bypass duct 30 connects into duct 26 above blower 24 and dampers 32 and 34 are positioned in duct 26 and duct 30, respectively, to control the relative flows in each duct and to ensure that the operation of oven 20 is not changed by such equipment. The gases flowing through duct 30 beyond damper 34 are cooled by suitable cooler 36 to condense the ethyl alcohol from the stack gases. Duct 38 connects from the outlet of cooler 36 to conduct the cooled gases into the lower portion of packed column 40. The gases flow upwardly through column and through suitable packing which functions to collect and coalesce the fine droplets of condensed alcohol and water. The condensed liquid is collected by the packing and drains to the lower portion of column 40 for discharge through line 42 under control of valve 44 which may be opened and closed responsive to a liquid level control mounted within column 40 or any other suitable means to ensure the discharge of the liquids from the bottom of column 40 through line 42 without discharging any of the gases therewith. The gases, free of the condensate are delivered from the top of column 40 to blower 46 and duct 48 into original duct 26. The improved method and apparatus as described will remove the pollutant ethyl alcohol from the stack gases discharged from a commercial bakery oven and collect them as a liquid together with the water removed from the gases so that the bakery no longer pollutes the atmosphere.

While it is considered of prime importance that the pollutant ethyl alcohol be removed from bakery oven stack gases, it is also very important to the owner of the bakery oven that the ethyl alcohol be recovered and sold to improve the financial position of the owner who is complying with the regulations on this type of discharge.

Figure 3:
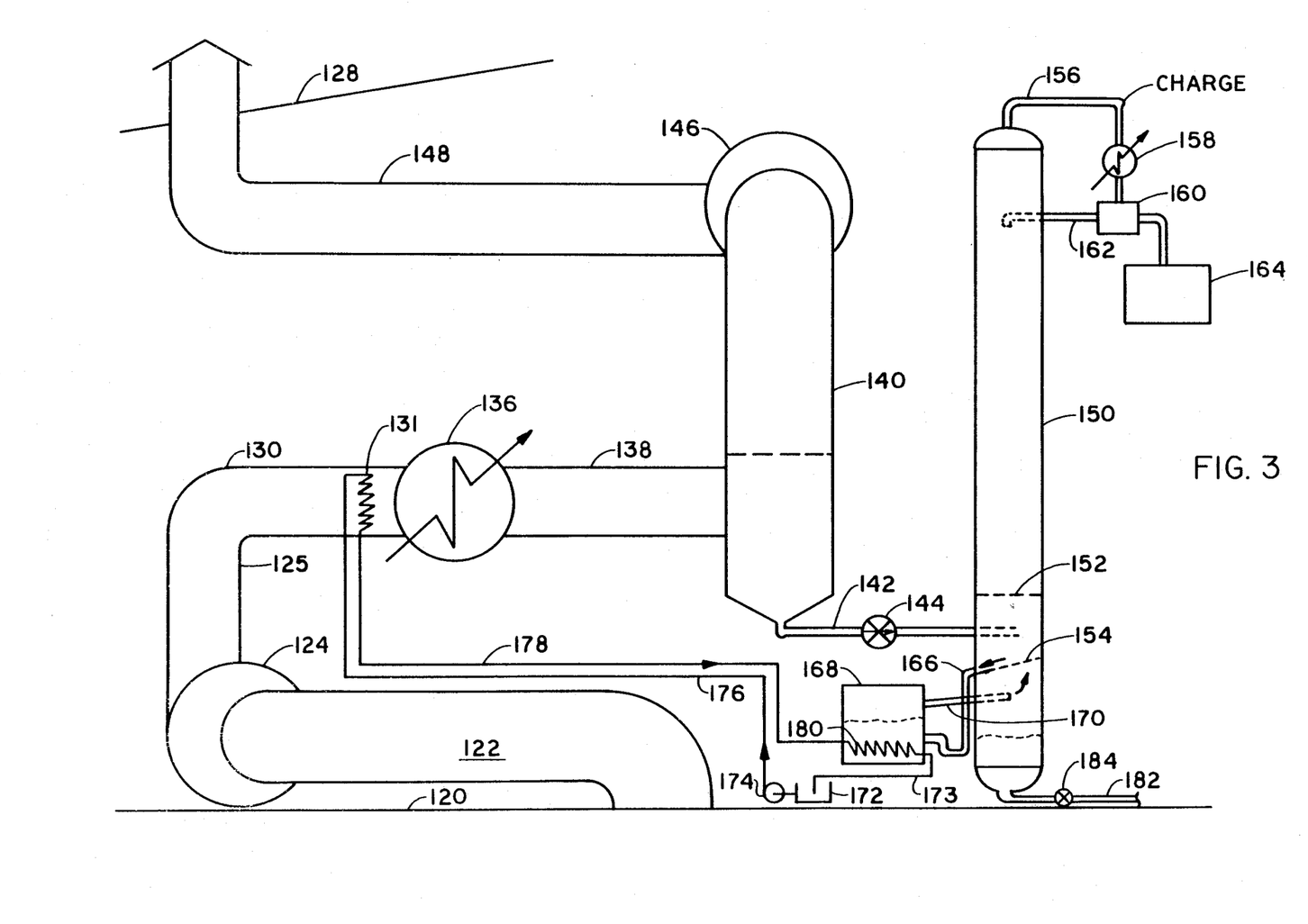
FIG. 3 is another schematic representation of an embodiment of the present invention which illustrates the improved separation of the ethyl alcohol and water.

In FIG. 3 a modified system is shown which utilizes the system shown in FIG. 2 (the components of which are hereinafter assigned the same number with the prefix 1) together with the step of separating and concentrating the ethyl alcohol. The oven 120 includes the stack 122 which connects to the stack blower 124 and the discharge of blower 124 is conducted through duct 125 through duct 130, past heat exchangers 131 and 136 to condense the ethyl alcohol. Duct 138 conducts the cooled stack gases into the lower portion of packed column 140 when through flow through the suitable packing wherein the fine droplets are coalesced and the condensed liquids are collected which drain to the lower portion of column 140 are discharged through line 142 under control of valve 144. The gases leaving the upper end of column 140 are drawn by blower 146 and deliver through duct 148 to stack 149 which extends through roof 128 and discharges the nonpolluting stack gases to the atmosphere.

The ethyl alcohol is processed to separate the water therefrom so that it has a concentration of approximately 95% while is a saleable concentration of the alcohol. This is accomplished in still column 150 by delivering the liquids Ln line 142 into the lower portion of column 150 between lower contacting tray 152 and liquid collecting tray 154. The portion of column 150 is provided with a plurality of gas-liquid contacting trays (not shown) above tray 152 and the gases are discharged from the upper end of column 150 through line 156. In order to provide an improved concentration of the alcohol, a reflux is provided to the upper end of still column 150 by cooling the gases flowing through line 156 in cooler 158 and flowing at least a part of the condensed liquid from collection drum 160 through line 162 into the upper portion of still column 150. This reflux liquid will flow downwardly in column to assist in the removal of the alcohol from the water. The remaining liquid from drum 160 is discharged into container 164 and gases are vented from drum 160. The liquid collecting on tray 154 is drained through line 166 into reboiler 168 and vapors generated therein are discharged into still column 150 through line 170 at a position below tray 154. Reboiler 168 is heated by the circulation of a heating medium from tank 172 through pump 174, line exchanger 131, through return line 178 into heating coil 180 within reboiler 168 and returned to tank 172 through line 173. The water is discharged from the bottom of still column 150 through line 182 under suitable control valve 184, such as a liquid level control valve, to a drain.

Figure 4:
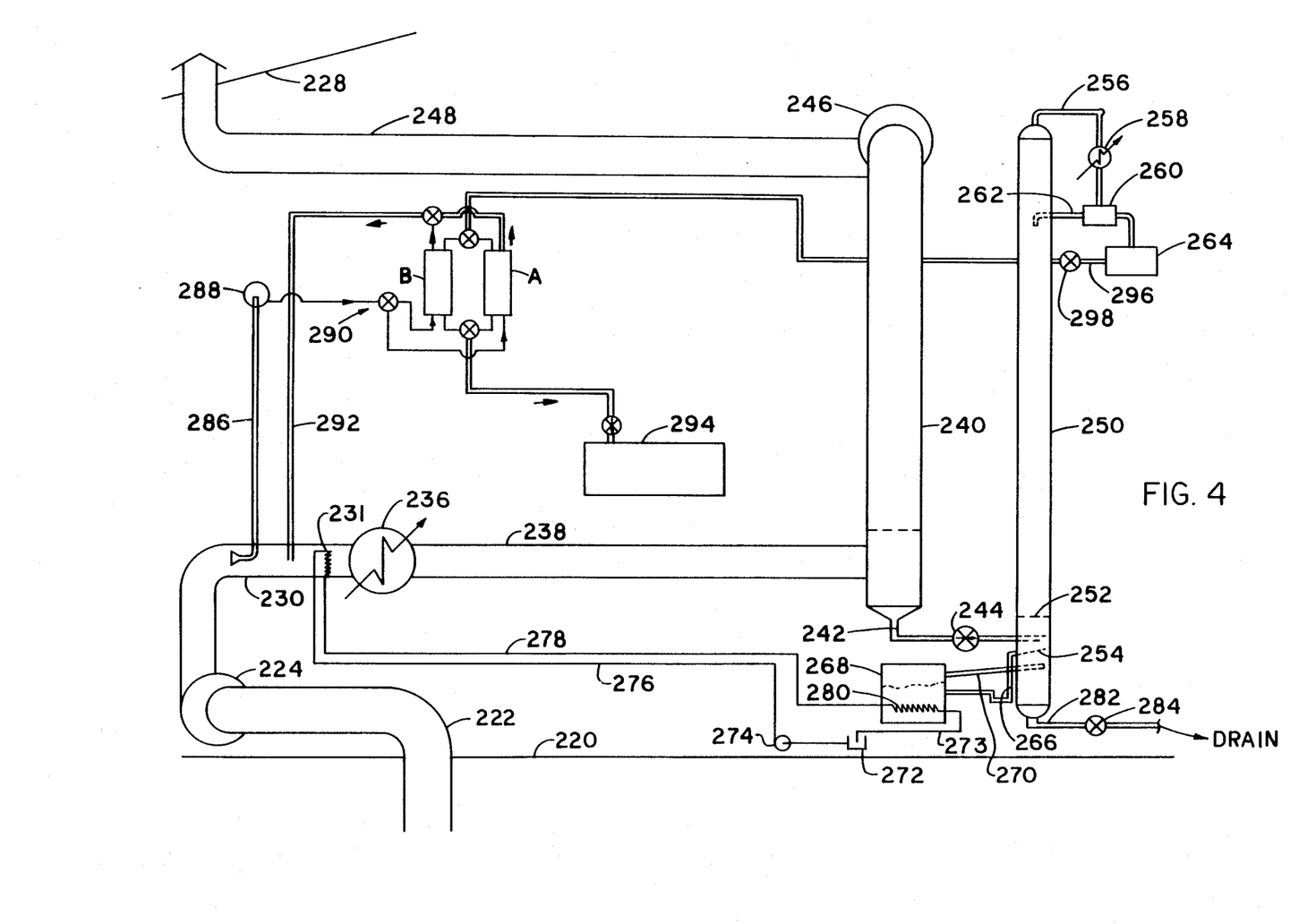
FIG. 4 is still another schematic representation of another embodiment of the present invention in which the recovered ethyl alcohol is concentrated to a greater degree.

FIG. 4 illustrates a process similar to FIG. 3 except that additional equipment is utilized to provide a higher degree of concentration of the ethyl alcohol. With the apparatus illustrated, it is believed possible to obtain of the alcohol to a level of 99%. In describing the apparatus illustrated in FIG. 4 the same numbers are used as were used in the above description of FIG. 3 except that they will include the prefix 2. The stack gases from bakery oven 220 are discharged through stack 222 and blower into duct 230 where they pass reboiler heat exchanger 231 and cooler 236. The cooled gases then pass through duct 238 into the lower portion of packed column 240. The packing in column 240 coalesce the fine droplets of the liquid condensed by the cooling and the liquid s are separated from the other stack gases and drain to the lower portion of column 240 from which they are discharged through line 242 under control of valve 244 into still column 250 at a position between lower gas-liquid contacting tray 252 and liquid collecting tray 254. The separated gases are discharged from packed column 240 through blower 246 and are discharged therefrom through stack 248 and roof 228 into the atmosphere. Reboiler 268 provides the heat necessary for heating liquids in the lower portion of still column 250. Liquids collecting on tray 254 are withdrawn from still column 250 and delivered into reboiler 268 and vapors generated therein are returned to still column 250 under tray 254 through line 270. Heat in reboiler is provided by liquid circulated by pump 274 from tank 272 through line 276, heat exchanger 231, line 278, heat exchanger coil 280 within the lower portion of reboiler 268 and are returned to tank 272 through line 273. The reflux to the upper end of still column 250 is provided by passing gases through line 256 and cooler 258 so that liquids condensed by the cooling are collected in collection drum 260 and at least a portion thereof are returned through line 262 to the upper portion of still column 250. Any excess liquids are delivered to container 264 and can be recycled to reboiler or used as reflux makeup. The concentrated ethyl alcohol (approximately 95% concentration) are delivered from container 264 through discharge line 296 under control of valve 298 into the illustrated molecular sieve drying system.

The additional concentration is achieved in the FIG. 4 apparatus by the utilization of one of the molecular sieves A or B to dry the alcohol flowing into the drying system while the other molecular sieve is being regenerated by bleeding a regeneration gas stream from duct 230 and conducting it through line 286, blower 288 through the molecular sieve valving system 290 and return through line 292 to duct 230. Valving system is suitably controlled so that when the molecular sieve receiving the alcohol for drying is becoming saturated, the valving is switched to conduct the alcohol into the just regenerated unit and to conduct the hot regeneration gases to the saturated unit. Such switching may be timed or made responsive to the approach of saturation conditions in the units by suitable sensing and control elements. With the additional drying of the molecular sieve system illustrated and described, the ethyl alcohol discharged therefrom to storage tank 294 will have a concentration of approximately 99%.

It is believed that concentrating the ethyl alcohol results in a more valuable product which is justified since the heat of the stack gases is used in the regeneration portion of the drying system. Thus the present invention not only solves the problem of removing the pollutant ethyl alcohol from the stack gases of a commercial bakery oven to comply with regulations controlling discharge of pollutants into the atmosphere but a valuable product is recovered which may be sold to minimize the expense of such compliance.

It should be noted that in all of the methods and apparatus shown and described herein, there should also be included suitable means such as dampers and controls for the blowers so that the conditions in the bakery oven can be maintained without changing the pressure or temperature or other operating condition therein as a result of the processing of the stack gases from the oven.

While the present invention has been described as having particular application to the treating of the stack gases from commercial bakery ovens, it should be noted that it could be used to treat similar stack gases originating from a different source to remove the ethyl alcohol pollutant from such stack gases.

What is claimed is:

1. The method of removing ethyl alcohol from commercial bakery oven stack gases including the steps of
    cooling the stack gases to condense the ethyl alcohol gases into liquid form,
    coalescing and collecting the condensed ethyl alcohol from the stack gases,
    separating the collected ethyl alcohol from the stack gases, and
    discharging the stack gases to the atmosphere free of any substantial quantity of ethyl alcohol.

2. The method as set forth in claim I wherein the condensed ethyl alcohol includes water condensed from the stack gases by the cooling step and including the step of
    separating the condensed ethyl alcohol from the water condensed from the stack gases.

3. The method as set forth in claim 2 wherein said water-alcohol separating step includes
    distilling the combined ethyl alcohol from the water mixture condensed from the stack gases to concentrate the alcohol to approximately 95 percent by volume.

4. The method as set forth in claim 3 including the step of
    utilizing the heat in the stack gases before cooling to provide heat for vaporizing the liquids in said distilling step.

5. The method as set forth in claim 4 including the steps of
    cooling the gases passing off the top of the still column to condense liquid therefrom, and
    returning the condensed liquid to the top of the still column as a reflux liquid.

6. The method as set forth in claim 3 including the further step of
    passing the distilled ethyl alcohol through a molecular sieve to increase its concentration to approximately 99 percent by volume.

7. The method as set forth in claim 6 including the further steps of
    bleeding a portion of the stack gases prior to cooling from the stack, and
    flowing such stack gases bleed through the molecular sieve as a regeneration gas to regenerate the molecular sieve after discontinuing the passing of the distilled ethyl alcohol therethrough.

8. The method as set forth in claim 7 wherein
    at least two molecular sieves are utilized and the flow of distilled ethyl alcohol and of regeneration gases are alternated through said two molecular sieves to maintain one molecular sieve on a regeneration cycle with the other molecular sieve on a drying cycle for drying of the distilled ethyl alcohol at all times.

9. The method as set forth in claim 7 wherein
    two molecular sieve units are utilized and the flow of ethyl alcohol and the flow of regeneration gases are controlled so that the ethyl alcohol alternately flows through one unit while the other unit is being regenerated.

10. The method of treating hot stack gases from a bakery oven containing ethyl alcohol, water and other gases including the steps of
    cooling the hot stack gases to condense the ethyl alcohol and water as liquids therefrom,
    coalescing and collecting the liquids condensed as a result of cooling said stack gases, and
    separating the condensed liquids from the remaining stack gases.

11. The method according to claim 10 including the steps of
    concentrating the ethyl alcohol in said separated liquids, and heating said condensed liquids with said hot stack gases prior to the cooling step in said concentrating step.

* * * * *

REEXAMINATION CERTIFICATE (2961th)

United States Patent [19]

Peck

[11] B1 4,834,841
[45] Certificate Issued Jul. 30, 1996

[54] METHOD FOR TREATING BAKING OVEN STACK GASES

[76] Inventor: Kenneth W. Peck, 13725 SW. 78 Ct., Miami, Fla. 33158

Reexamination Request:
No. 90/003,763, Mar. 21, 1995

Reexamination Certificate for:
| | |
|---|---|
| Patent No.: | 4,834,841 |
| Issued: | May 30, 1989 |
| Appl. No.: | 103,299 |
| Filed: | Oct. 1, 1987 |

[51] Int. Cl.[6] .................... B01D 3/14; B01D 5/00; B01D 15/00; C07C 29/80
[52] U.S. Cl. .................... 203/19; 203/25; 203/27; 203/41; 203/100; 203/DIG. 8; 203/DIG. 13; 55/97; 55/269; 126/300; 202/176; 202/202; 210/673; 210/677; 568/916
[58] Field of Search .................... 203/19, DIG. 13, 203/21, 25, 27, 40, 41, 100, DIG. 8; 202/153, 163, 176, 182; 126/202, 299 R, 300, 301; 55/269; 96/108, 121, 126, 130, 141, 143; 426/523; 568/913, 916

[56] References Cited

U.S. PATENT DOCUMENTS

| | | | |
|---|---|---|---|
| 1,577,534 | 3/1926 | Miller | 55/269 |
| 2,743,529 | 5/1956 | Hayes | 126/299 R |
| 3,122,486 | 2/1964 | Skarstrom | 203/41 |
| 3,124,438 | 3/1964 | Lavery | 55/62 |
| 3,151,607 | 10/1964 | Brouillard | 126/299 R |
| 3,369,371 | 2/1968 | Holly et al. | 62/54 |
| 3,396,515 | 8/1968 | Wright | 55/269 |
| 3,729,387 | 4/1973 | Naschke et al. | 203/19 |
| 3,762,394 | 10/1973 | Newcomer | 126/300 |
| 3,890,207 | 6/1975 | Chapman et al. | 203/DIG. 8 |
| 3,963,466 | 6/1976 | Hynes | 55/269 |
| 4,101,299 | 7/1978 | Bertucci | 55/269 |
| 4,110,091 | 8/1978 | Daeschler et al. | 62/54 |
| 4,126,000 | 11/1978 | Funk | 60/648 |
| 4,216,903 | 8/1980 | Giuffre | 126/299 R |
| 4,265,088 | 5/1981 | Funk | 60/648 |
| 4,266,958 | 5/1981 | Cummings | 62/20 |
| 4,294,664 | 10/1981 | Anthony | 203/19 |
| 4,331,690 | 5/1982 | Bradshaw | 426/233 |
| 4,362,751 | 12/1982 | Dogliotti | 426/94 |
| 4,377,443 | 3/1983 | Tuck et al. | 203/8 |

(List continued on next page.)

FOREIGN PATENT DOCUMENTS

| | | |
|---|---|---|
| 1087929 | 3/1955 | France . |
| 242820 | 2/1987 | Germany . |
| 42787 | 9/1975 | Romania . |

OTHER PUBLICATIONS

Organic Chemistry, by Frank C. Whitmore, Aug. 1938 D. Van Nostrand Company, Inc., pp. 107 and 108.
Exhibit A—Submission of Prior Art References Dated Oct. 15, 1987.
Exhibit B—Examiner's Paper No. 3 Dated Jun. 14, 1988.
Exhibit C—Amendment Paper No. 4 Dated Sep. 8, 1988.
Exhibit D—Examiner's Paper No. 5 Dated Dec. 23, 1988.
Exhibit E—Examiner's Interview Summary Record Paper No. 6.
Exhibit F—Notice of Allowability Paper No. 7 Dated Jan. 31, 1989.
Exhibit G—Notice of Allowance and Issue Fee Due Dated Jan. 31, 1989.

*Primary Examiner*—Robert J. Warden

[57] ABSTRACT

The improved method and apparatus treats the stack gases from a commercial bakery oven to remove and recover pollutants, specifically ethyl alcohol. The method includes the steps of cooling the stack gases and passing the cooled gases through a packed column to condense the water and ethyl alcohol and if the ethyl alcohol is to be recovered drying the ethyl alcohol by distillation and by absorption of the water therefrom by a molecular sieve. The apparatus includes blowers and controls to maintain the normal flow of gases from the oven so that the removal and recovery of the ethyl alcohol from the stack gases does not interfere or change the baking conditions of the oven. This may be accomplished by a system of dampers or by controlling the discharge rate of the blowers used.

U.S. PATENT DOCUMENTS

| | | | |
|---|---|---|---|
| 4,407,662 | 10/1983 | Ginder | 55/33 |
| 4,454,100 | 6/1984 | Faatz | 423/210 |
| 4,484,451 | 11/1984 | Darm | 55/269 |
| 4,556,460 | 12/1985 | Robertson et al. | 203/19 |
| 4,608,065 | 8/1986 | Lai | 55/269 |
| 4,616,562 | 10/1986 | Kuechler | 126/299 R |
| 4,834,841 | 5/1989 | Peck . | |

B1 4,834,841

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

* * * * *